(12) United States Patent
Allison et al.

(10) Patent No.: US 11,590,140 B1
(45) Date of Patent: Feb. 28, 2023

(54) FORMULATION FOR ALLEVIATING VEISALGIA SYMPTOMS

(71) Applicant: PSR Brands, LLC, Houston, TX (US)

(72) Inventors: Jason Kelly Allison, Houston, TX (US); Guillermo A. Amtmann, Houston, TX (US); John Burton Steele, Houston, TX (US)

(73) Assignee: PSR Brands, LLC, Houston, TX (US)

( * ) Notice: Subject to any disclaimer, the term of this patent is extended or adjusted under 35 U.S.C. 154(b) by 382 days.

(21) Appl. No.: 16/596,560

(22) Filed: Oct. 8, 2019

Related U.S. Application Data

(60) Provisional application No. 62/742,659, filed on Oct. 8, 2018.

(51) Int. Cl.
| | |
|---|---|
| *A61K 31/522* | (2006.01) |
| *A61K 31/7034* | (2006.01) |
| *A61K 36/35* | (2006.01) |
| *A61K 31/194* | (2006.01) |
| *A61K 36/9068* | (2006.01) |
| *A61K 33/06* | (2006.01) |
| *A61K 31/19* | (2006.01) |
| *A61K 33/14* | (2006.01) |

(52) U.S. Cl.
CPC ............ *A61K 31/522* (2013.01); *A61K 31/19* (2013.01); *A61K 31/194* (2013.01); *A61K 31/7034* (2013.01); *A61K 33/06* (2013.01); *A61K 33/14* (2013.01); *A61K 36/35* (2013.01); *A61K 36/9068* (2013.01)

(58) Field of Classification Search
CPC .. A61K 31/522; A61K 31/7034; A61K 36/35; A61K 31/194; A61K 36/9068; A61K 33/06; A61K 31/19; A61K 33/14
See application file for complete search history.

(56) References Cited

U.S. PATENT DOCUMENTS

| | | | | |
|---|---|---|---|---|
| 4,582,715 A | * | 4/1986 | Volpenhein | A23L 33/115 426/601 |
| 6,312,736 B1 | * | 11/2001 | Kelly | A61K 36/28 424/450 |
| 2006/0062859 A1 | * | 3/2006 | Blum | A61K 38/4873 424/725 |
| 2008/0057161 A1 | * | 3/2008 | Brucker | A23L 33/17 426/73 |
| 2015/0157672 A1 | * | 6/2015 | Cairns | A61K 36/53 424/195.17 |

OTHER PUBLICATIONS

PPN Launches "Diet Season" Anaheim, CA PRWeb Jun. 24, 2004.*
Sports Science Exchange 18(1); 2005).*

* cited by examiner

*Primary Examiner* — Shirley V Gembeh
(74) *Attorney, Agent, or Firm* — Baker Botts L.L.P.

(57) ABSTRACT

The embodiments of the present disclosure generally relate to a formulation for alleviating veisalgia symptoms. The formulation can comprise anhydrous caffeine, salicin, and valerian. The components can be delivered within a liquid medium and act synergistically to more effectively relieve veisalgia symptoms than when taken individually.

13 Claims, 1 Drawing Sheet

| INGREDIENT | AMOUNT PER CAN GRAMS | RELATIVE RATIO | RANGE OF INGREDIENTS | | | | | |
|---|---|---|---|---|---|---|---|---|
| | | | WIDE | | MEDIUM | | NARROW | |
| MAGNESIUM CHLORIDE | 0.010 | 0.200 | 0.001 | 0.1 | 0.005 | 0.02 | 0.0075 | 0.0125 |
| CAFFEINE ANHYDROUS | 0.050 | 1.000 | 0.005 | 0.5 | 0.025 | 0.1 | 0.0375 | 0.0625 |
| SALICIN (98%) | 0.123 | 2.460 | 0.0123 | 1.23 | 0.0615 | 0.246 | 0.09225 | 0.15375 |
| VALERIAN | 0.250 | 5.000 | 0.025 | 2.5 | 0.125 | 0.5 | 0.1875 | 0.3125 |
| GINGER (5% GINGEROLS) | 0.050 | 1.000 | 0.005 | 0.5 | 0.025 | 0.1 | 0.0375 | 0.0625 |
| CALCIUM LACTATE (CALCIUM SOURCE) | 0.033 | 0.660 | 0.0033 | 0.33 | 0.0165 | 0.066 | 0.02475 | 0.04125 |
| TRISODIUM CITRATE (SODIUM SOURCE) | 1.000 | 20.000 | 0.1 | 10 | 0.5 | 2 | 0.75 | 1.25 |
| POTASSIUM CITRATE (POTASSIUM SOURCE) | 0.300 | 6.000 | 0.03 | 3 | 0.15 | 0.6 | 0.225 | 0.375 |
| VIATECH (STEVIA) | 0.100 | 2.000 | 0.01 | 1 | 0.05 | 0.2 | 0.075 | 0.125 |
| | 1.816 | 1.916 | | | | | | |
| CITRIC ACID | 2.000 | 40.000 | 0.2 | 20 | 1 | 4 | 1.5 | 2.5 |
| SUCROSE | 55.00 | 1100.00 | 5.5 | 550 | 27.5 | 110 | 41.25 | 68.75 |
| GREEN COFFEE BEAN EXTRACT | 0.027 | 0.534 | 0.00267 | 0.267 | 0.01335 | 0.0534 | 0.020025 | 0.033375 |
| CALCIUM PANTOTHENATE-VITAMIN B5 | 0.013 | 0.267 | 0.001333 | 0.1333 | 0.006665 | 0.02666 | 0.009998 | 0.016663 |
| NIACINAMIDE | 0.027 | 0.534 | 0.00267 | 0.267 | 0.01335 | 0.0534 | 0.020025 | 0.033375 |
| PYRIDOXINE HCl-VITAMIN B6 | 0.003 | 0.053 | 0.000267 | 0.0267 | 0.001335 | 0.00534 | 0.002003 | 0.003338 |
| BIOTIN-VITAMIN B7 | 0.0002000 | 0.0040000 | 0.00002 | 0.002 | 0.0001 | 0.0004 | 0.00015 | 0.00025 |
| FOLIC ACID | 0.0000530 | 0.0010600 | 0.0000053 | 0.00053 | 2.65E-05 | 0.000106 | 3.98E-05 | 6.63E-05 |
| METHYLCOBALAMIN-VITAMIN B12 | 0.0000040 | 0.0000800 | 0.0000004 | 0.00004 | 0.000002 | 0.000008 | 0.000003 | 0.000005 |
| MIXED BERRY-NATURAL-COMAX-78.761 | 0.700 | 14.000 | 0.07 | 7 | 0.35 | 1.4 | 0.525 | 0.875 |
| GAMMA-AMINOBUTYRIC ACID (GABA) | 0.500 | 10.000 | 0.05 | 5 | 0.25 | 1 | 0.375 | 0.625 |
| SODIUM GLUCONATE | 0.200 | 4.000 | 0.02 | 2 | 0.1 | 0.4 | 0.15 | 0.25 |
| SODIUM BENZOATE | 0.142 | 2.840 | 0.0142 | 1.42 | 0.071 | 0.284 | 0.1065 | 0.1775 |
| POTASSIUM SORBATE | 0.142 | 2.840 | 0.0142 | 1.42 | 0.071 | 0.284 | 0.1065 | 0.1775 |

FORMULATION FOR ALLEVIATING VEISALGIA SYMPTOMS

CROSS REFERENCE TO RELATED APPLICATIONS

The present application claims priority to and the benefit of U.S. Provisional Patent Application Ser. No. 62/742,659 filed on Oct. 8, 2018, titled "FORMULATION FOR ALLEVIATING VEISALGIA SYMPTOMS". This reference is incorporated herein in its entirety.

FIELD

The present disclosure generally relates to a formulation for alleviating veisalgia symptoms.

BACKGROUND

Most adults have suffered from the effects of veisalgia at some point in their lifetime. Veisalgia is a medical term to describe the unpleasant aftereffects of alcohol consumption, commonly referred to as a hangover.

While the physiological processes which lead to veisalgia are poorly understood, several effects of alcohol consumption may be the. It is thought that various factors, such as hormonal alterations, decrease in the availability of glucose, metabolism of ingredients into toxic substances, metabolic acidosis, vasodilation, poor sleep (or lack thereof), and dehydration just to name a few can all contribute to veisalgia.

While many treatments have been proposed in conjunction with numerous folk remedies, an effective formulation of ingredients is not known of in the art.

The present disclosure provides a formulation of components for the effective alleviation of vesalgia symptoms.

BRIEF DESCRIPTION OF THE DRAWINGS

The detailed description will be better understood in conjunction with the accompanying drawing as follows:

The FIGURE shows various ranges of the ingredients usable by the formulation of the present disclosure.

The embodiments of the present disclosure are detailed below with reference to the listed FIGURE.

DETAILED DESCRIPTION OF THE EMBODIMENTS

Before explaining the present disclosure in detail, it is to be understood that the disclosure is not limited to the specifics of particular embodiments as described and that it can be practiced, constructed, or carried out in various ways.

While embodiments of the disclosure have been shown and described, modifications thereof can be made by one skilled in the art without departing from the spirit and teachings of the disclosure. The embodiments described herein are exemplary only, and are not intended to be limiting.

Specific structural and functional details disclosed herein are not to be interpreted as limiting, but merely as a basis of the claims and as a representative basis for teaching persons having ordinary skill in the art to variously employ the present embodiments. Many variations and modifications of embodiments disclosed herein are possible and are within the scope of the present disclosure.

Where numerical ranges or limitations are expressly stated, such express ranges or limitations should be understood to include iterative ranges or limitations of like magnitude falling within the expressly stated ranges or limitations.

The use of the word "a" or "an" when used in conjunction with the term "comprising" in the claims and/or the specification may mean "one," but it is also consistent with the meaning of "one or more," "at least one," and "one or more than one."

The word "about" means plus or minus 5% of the stated number.

The use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

When methods are disclosed or discussed, the order of the steps is not intended to be limiting, but merely exemplary unless otherwise stated.

Accordingly, the scope of protection is not limited by the description herein, but is only limited by the claims which follow, encompassing all equivalents of the subject matter of the claims. Each and every claim is hereby incorporated into the specification as an embodiment of the present disclosure. Thus, the claims are a further description and are an addition to the embodiments of the present disclosure.

The inclusion or discussion of a reference is not an admission that it is prior art to the present disclosure, especially any reference that may have a publication date after the priority date of this application. The disclosures of all patents, patent applications, and publications cited herein are hereby incorporated by reference, to the extent they provide background knowledge; or exemplary, procedural or other details supplementary to those set forth herein.

The embodiments of the present disclosure generally relate to a formulation for alleviating veisalgia symptoms.

The formulation can comprise anhydrous caffeine, salicin, and valerian.

Caffeine is a bitter, white crystalline purine, and a methylxanthine alkaloid. It is found in the seeds, nuts, or leaves of a number of plants. The most well-known source of caffeine is the coffee bean. Beverages containing caffeine, such as coffee or colas are often ingested to promote wakefulness and/or to improve performance. Caffeine acts as a central nervous system stimulant and is useful for treating drowsiness, headaches, and migraines. Caffeine can increase blood pressure either by increasing adrenalin, or by acting as a vasoconstrictor. Caffeine stimulates respiration, and caffeine also acts to stimulate gastric secretion.

Salicin is a glucoside which is naturally produced by plants such as willow. It is converted to salicylic acid when metabolized and can have effects such as those of aspirin. Salicin has the added benefit of providing pain relief without affecting gastrointestinal mucosa or blood clotting. This has the synergistic benefit of providing aspirin-like relief without counteracting the effects of caffeine.

Valerian is a flowering plant, whose extracts are known to have beneficial effects. When referencing valerian in the present disclosure, any extract of the valerian plant is what is intended. While commonly used for sleep disorders, valerian also acts as an anxiolytic by modulating GABA receptors.

Various ingredients can be added to the formulation for taste. Ingredients can include, but are not limited to: *stevia*, citric acid, sucrose, flavors (natural and unnatural), fruit flavors, GABA, sodium gluconate, and the like. Flavonoids, or polyphenolic compounds with a flavan nucleus, can act in conjunction with salicin to further provide pain relief benefits. Flavanoids occur naturally within plants and can be added to the composition of the present disclosure via natural fruit and vegetable flavors.

Ingredients such as sodium benzoate and potassium sorbate can be added as preservatives.

Various vitamins can be added to the formulation if desired. Exemplary vitamins include, but are not limited to: green coffee bean extract, Calcium Pantothenate-Vitamin B5, Niacinamide, Pyridoxine HCl-Vitamin B6, Biotin-Vitamin B7, Folic Acid, and Methylcobalamin-Vitamin B12.

Additional ingredients that can bolster the efficacy of the formulation include magnesium chloride, calcium lactate, trisodium citrate, and potassium citrate. These ingredients act to replenish magnesium, calcium, sodium, and potassium in the body. Various physiological processes require these electrolytes within the body, and by rapidly delivering them, the alleviation of veisalgia is aided.

In embodiments, ginger can be added to control nausea. The formulation acts synergistically to promote the absorption and effects of ginger. Further, caffeine and salicin act synergistically to more effectively scavenge reactive oxygen species, leading to improved immediate and long term health benefits.

Turning now to the FIGURE, the FIGURE shows various ranges of the ingredients usable by the formulation of the present disclosure.

While the present disclosure emphasizes the embodiments, it should be understood that within the scope of the appended claims, the disclosure might be embodied other than as specifically described herein.

What is claimed is:

1. A formulation comprising:
   a. anhydrous caffeine;
   b. salicin; and
   c. valerian; and
   wherein the relative weight ratios of anhydrous caffeine:salicin:valerian is 1:1.2-3.8:2.5-8, and
   wherein the components act synergistically to alleviate veisalgia symptoms.

2. The formulation of claim 1, further comprising magnesium chloride.

3. The formulation of claim 1, further comprising ginger.

4. The formulation of claim 1, further comprising calcium lactate.

5. The formulation of claim 1, further comprising trisodium citrate.

6. The formulation of claim 1, further comprising potassium citrate.

7. The formulation of claim 1, wherein the relative weight ratios of anhydrous caffeine:salicin:valerian is 1:2-3:4-6.

8. The formulation of claim 1, wherein the relative weight ratios of anhydrous caffeine:salicin:valerian is 1:about 2.46:about 5.

9. The formulation of claim 1, further comprising at least one of:
   a. *stevia*;
   b. citric acid;
   c. sucrose;
   d. green coffee bean extract;
   e. Calcium Pantothenate-Vitamin B5;
   f. Niacinamide;
   g. Pyridoxine HCl-Vitamin B6;
   h. Biotin-Vitamin B7;
   i. Folic Acid;
   j. Methylcobalamin-Vitamin B12;
   k. Mixed Berry-Natural-COMAX-78.761;
   l. Gamma-Aminobutyric Acid (GABA);
   m. Sodium Gluconate;
   n. Sodium Benzoate; or
   o. Potassium Sorbate.

10. A formulation comprising:
    a. anhydrous caffeine;
    b. salicin;
    c. valerian; and
    d. ginger;
    wherein the relative weight ratios of anhydrous caffeine:salicin:valerian is 1:1.2-3.8:2.5-8, and
    wherein the components act synergistically to alleviate veisalgia symptoms.

11. A formulation comprising:
    a. anhydrous caffeine;
    b. salicin;
    c. valerian;
    d. magnesium chloride;
    e. ginger;
    f. calcium lactate;
    g. trisodium citrate; and
    h. potassium citrate
    wherein the relative weight ratios of anhydrous caffeine:salicin:valerian:magnesium chloride:ginger:calcium lactate:trisodium citrate:potassium citrate is about 1:1.2-3.8:2.5-8:0.1-0.4:1:0.3-1.5:10-35:3-10.

12. The formulation of claim 11, wherein the relative weight ratios of anhydrous caffeine:salicin:valerian:magnesium chloride:ginger:calcium lactate:trisodium citrate:potassium citrate is about 1:2-3:4-6:0.18-0.22:1:0.54-0.88:16-22:4.8-7.2.

13. The formulation of claim 11, wherein the relative weight ratios of anhydrous caffeine:salicin:valerian:magnesium chloride:ginger:calcium lactate:trisodium citrate:potassium citrate is about 1:2.46:5:0.2:1:0.660:20:6.

* * * * *